United States Patent [19]

Schwindeman et al.

[11] Patent Number: 4,596,883

[45] Date of Patent: Jun. 24, 1986

[54] HERBICIDALLY ACTIVE SUBSTITUTED DIPHENYL ETHERS

[75] Inventors: James A. Schwindeman, Canal Fulton; Horng-Jau Lin, Wadsworth, both of Ohio

[73] Assignee: PPG Industries, Inc., Pittsburgh, Pa.

[21] Appl. No.: 628,088

[22] Filed: Jul. 5, 1984

[51] Int. Cl.[4] .............................................. C07C 79/46
[52] U.S. Cl. ...................................... 560/21; 562/435; 562/463; 560/53; 558/415; 71/105; 71/107; 71/111; 558/405
[58] Field of Search .................... 560/21, 53; 562/435, 562/463; 260/465 D; 71/105, 107, 111

[56] References Cited

U.S. PATENT DOCUMENTS 4,093,446  6/1978  Bayer et al. ........................... 560/21
4,344,789  8/1982  Krass ..................................... 560/21

*Primary Examiner*—Paul J. Killos
*Attorney, Agent, or Firm*—Edward J. Whitfield

[57] ABSTRACT

The invention relates to certain herbicidally active substituted diphenyl ether derivatives, herbicidal compositions of the same and the use thereof for preemergence and postemergence control of noxious plants, i.e., weeds.

6 Claims, No Drawings

HERBICIDALLY ACTIVE SUBSTITUTED DIPHENYL ETHERS

FIELD OF THE INVENTION

This invention relates to certain herbicidally active substituted diphenyl ether derivatives, formulations thereof and their use for the control of noxious plants, i.e., weeds.

DESCRIPTION OF THE INVENTION

This invention provides herbicidally active substituted diphenyl ether compounds represented by the Formula I:

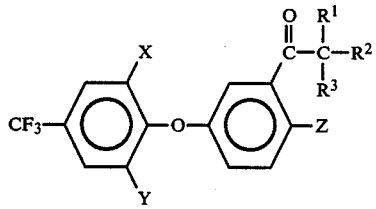

wherein:

X and Y are hydrogen or halogen provided that at least one of X or Y is halogen;

Z is nitro, halogen or cyano; $R^1$, $R^2$ and $R^3$ are individually selected from hydrogen, cyano, up to $C_4$ alkyl, haloalkyl alkoxy or alkoxyalkyl, up to $C_4$ alkenyl or alkynyl, phenyl or phenyl substituted with halogen, cyano, nitro or haloalkyl, provided that at least one of $R^1$, $R^2$ or $R^3$ is —COOR$^4$ wherein $R^4$ is hydrogen, up to $C^4$ alkyl, haloalkyl or alkoxy, mono- or dialkylamino, cyano or an agronomically suitable salt species selected from alkali metal ion, ammonium or substituted ammonium ion.

Suitable alkyl radicals of which the various 'R' groups are representative include methyl, ethyl, n-propyl, iso-propyl, n-butyl, t-butyl or iso-butyl. Choromethyl, chloroethyl, dichloroethyl, bromomethyl, bromoethyl, trifluoromethyl, trifluoroethyl, trichloromethyl and the like are exemplary haloalkyls. As examples of alkoxy radicals there may be mentioned methoxy, ethoxy, propoxy, or the like. Mono or dialkyl amino groups include methylamino, dimethylamino, methylethylamino, diethylamino or the like. Halogens represented by X, Y, and Z include bromine, chlorine or fluorine. Sodium, potassium or lithium, preferably sodium or potassium, are exemplary of alkali metal ions represented by $R^4$.

Preferred compounds of the Formula I are those wherein X is halogen, e.g., fluorine or chlorine; Y is hydrogen; Z is nitro; or halogen; and $R^1$, $R^2$ and $R^3$ are hydrogen or —COOR$^4$ wherein $R^4$ is alkyl.

Compounds of the Formula I may be prepared using techniques known to and starting materials available to the art. For example, a Formula I compound may be prepared by reacting an appropriately substituted phenoxybenzoyl halide of the Formula II:

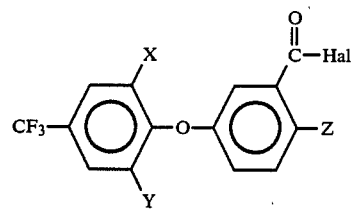

wherein X, Y and Z are as previously defined and Hal is halogen, e.g., chlorine or bromine, with an approximately substituted alkali metal salt of a compound of the Formula III:

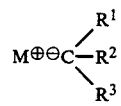

wherein $R^1$, $R^2$ and $R^3$ are as previously defined and M is alkali metal, e.g., sodium or magnesium.

The following Examples are illustrative of the preparation of certain compound of this invention.

EXAMPLE I

Preparation of: Diethyl 2-[5-(2-chloro-4-trifluoromethylphenoxy)-2-nitrobenzoyl]-2-methylmalonate To a stirred, cooled (0°–5° C.) suspension of 2.55 grams (0.0105 mole) of the ethyoxymagnesium salt of diethyl methylmalonate in 20 milliliters of anhydrous diethyl ether was added dropwise 3.80 grams (0.01 mole) of 5-[2-chloro-4-trifluoromethylphenoxy)-2-nitrobenzoyl]chloride in 10 milliliters of anhydrous diethyl ether. The reaction mixture was allowed to warm to ambient temperature and stirring was continued an additional hour. The reaction mixture was poured into a beaker and the reaction flask was rinsed with 20 milliliters of anhydrous diethyl ether which rinsings were combined with the reaction mixture. Ten milliliters of water were added and the mixture was neutralized with 6 Normal sulfuric acid. The organic layer was separated and washed consecutively with 10 milliliter portion of water, 5 percent aqueous sodium bicarbonate solution, water and saturated aqueous sodium chloride solution. After drying over anhydrous sodium sulfate, solvent was evaporated under reduced pressure affording a syrupy residue which was further dried under vacuum (0.1 mm Hg) affording 4.82 grams of material identified by NMR and IR analyses as the desired product.

EXAMPLE II

Preparation of: Diethyl2-[5-(2-chloro-4-trifluoromethylphenoxy)-2-nitrobenzoyl]-2-phenylmalonate To a suspension of 0.7 gram (0.029 mole) of sodium hydride (added as a 50 weight percent oil dispersion washed with hexane before use) in 25 milliliters of tetrahydrofuran was added 6.3 grams (0.0266 mole) of diethyl phenylmalonate at 0°–5° C. The mixture was stirred at ambient temperature for 20 minutes, cooled to 0°–5° C. and 9.2 grams (0.0242 mole) of 5-(2-chloro-4-trifluoromethylphenoxy)-2-nitrobenzoyl chloride in 40 milliliters of tetrahydrofuran was added dropwise.

After stirring for 18 hours at room temperature, the mixture was allowed to stand quiescent until precipitation was complete. The mixture was then filtered and the filtrate was evaporated under reduced pressure affording 14.09 grams of material identified by NMR analysis as the desired product.

EXAMPLE III

Preparation of: Dimethyl 2-[5-(2-chloro-4-trifluoromethylphenoxy)-2-chlorobenzoyl]malonate To a gently refluxing mixture of 0.015 mole of the methoxymagnesium salt of dimethyl malonate in 50 milliliters of anhydrous diethylether was added 5.0 grams (0.0135 mole) of 5-(2-chloro-4-trifluoromethylphenoxy)-2-chlorobenzoyl chloride in 20 milliliters of anhydrous diethylether at such a rate to maintain gentle reflux. After refluxing for two hours the reaction mixture was cooled to room temperature and acidified with a 90:10 V/V solution of water:acetic acid. (The white precipitate floating in the reaction mixture rapidly dissolved upon acidification). The mixture was transferred to a separatory funnel, the pale orange organic layer was drawn-off and the aqueous layer was extracted with 3×100 milliliter portions of anhydrous diethyl ether, the extracts being combined with the previously drawn-off organic layer. Subsequently drying over anhydrous magnesium sulfate, filtration and solvent stripping afforded 6.74 grams of an orange oil confirmed by IR and NMR analyses as the desired product.

EXAMPLE IV

Preparation of: Ethyl 2-[5-(2-chloro-4-trifluoromethylphenoxy)-2-chlorobenzoyl] cyanoacetate To a suspension of 0.24 gram (0.01 mole) of sodium hydride in 15 milliliters of dry tetrahydrofuran was added dropwise 0.70 gram (0.006 mole) of ethyl cyanoacetate dissolved in 5 milliliters of dry tetrahydrofuran. After stirring for 30 minutes at room temperature (by which time all gas evolution had ceased), 1.0 gram (0.0027 mole) of 5-(2-chloro-4-trifluoromethylphenoxy)-2-nitrobenzolyl chloride in 4 milliliters of dry tetrahydrofuran was added dropwise. The reaction mixture was then heated to reflux, refluxed for 2 hours and then cooled to about 0° C. The reaction was quenched by the dropwise addition of 10 milliliters of pH 4 buffer solution, resulting in vigorous gas evolution and considerable frothing. The reaction mixture was then adjusted to pH 4 by addition of about 30 milliliters of 5 percent aqueous hydrochloric acid solution, transferred to a separatory funnel and extracted with 70 milliliter portions of ethyl acetate. The combined organic extracts were dried over anhydrous magnesium sulfate, filtered and concentrated in vacuo affording 1.69 grams of orange oil confirmed by NMR and MS analyses as the desired product.

EXAMPLE V

Preparation of: Ethyl 2-[5-(2-chloro-4-trifluoromethylphenoxy)-2-nitrobenzoyl]cyanoacetate To a suspension of 0.41 gram (0.017 mole) of sodium hydride in 50 milliliters of dry tetrahydrofuran was added dropwise over a 15 minute period, 1.70 grams (0.015 mole) of ethyl cyanoacetate dissolved in 10 milliliters of dry tetrahydrofuran. After stirring for 30 minutes at room temperature (by which time all gas evolution had ceased), 4.5 grams (0.0118 mole) of 5-(2-chloro-4-trifluoromethylphenoxy)-2-nitrobenzoyl chloride dissolved in 20 milliliters of dry tetrahydrofuran was added dropwise, over a 27 minute period. The reaction mixture was stirred at room temperature for one hour, heated to reflux and refluxed for one hour, after which it was cooled to room temperature, poured into a separatory funnel containing 200 milliliters of 5 percent aqueous hydrochloric acid solution and extracted with 3×150 milliliter portions of ethyl acetate. The combined organic extracts were dried over anhydrous magnesium sulfate, filtered and the filtrate concentrated in vacuo affording 5.10 grams of an orange oil confirmed by NMR and MS analyses as the desired product.

EXAMPLE VI

Preparation of: Diethyl 2-[5-(2-chloro-4-trifluoromethylphenoxy)-2-nitrobenzoyl]-2-allyl malonate To a stirred suspension of 0.18 gram (0.0075 mole) of sodium hydride in 8 milliliters of dry tetrahydrofuran was added dropwise, over a 30 minute period, 1.24 grams (0.0062 mole) of diethyl allyl malonate dissolved in 6 milliliters of dry tetrahydrofuran, and stirred an additional 30 minutes at room temperature. Then, 2.0 grams (0.0053 mole) of 5-(2-chloro-4-trifluoromethylphenoxy)-2-nitrobenzoyl chloride dissolved in 15 milliliters of dry tetrahydrofuran was added dropwise. The reaction mixture was stirred for 30 minutes at room temperature and heated to reflux and maintained at reflux for 45 minutes. After cooling to room temperature, the reaction mixture was carefully quenched with 5 percent aqueous hydrochloric acid solution, transferred to a separatory funnel, diluted with 100 milliliters of 5 percent aqueous hydrochloric acid solution and extracted with 3×100 milliliter portions of methylene chloride. The combined organic extracts were dried over anhydrous magnesium sulfate, filtered and the filtrate concentrated in vacuo affording 3.07 grams of a reddish brown oil confirmed by NMR and MS analyses as the desired product.

EXAMPLE VII

Preparation of: t-Butylethyl 2-[(2-chloro-4-trifluoromethylphenoxy)-2-nitrobenzoyl]malonate To a stirred suspension of 0.38 gram (0.016 mole) of sodium hydride in 25 milliliters of dry tetrahydrofuran was added dropwise 2.5 grams (0.0133 mole) of t-butylethyl malonate. After stirring for 30 minutes following addition of the t-butylethyl malonate, 2.28 grams (0.006 mole) of 5-(2-chloro-4-trifluoromethylphenoxy)-2-nitrobenzoyl chloride dissolved in 20 milliliters of tetrahydrofuran was added dropwise, mild gas evolution being observed. After stirring for 30 minutes, the reaction mixture was heated to reflux, maintained at reflux for 45 minutes, cooled to room temperature, carefully quenched with 100 milliliters of 5 percent aqueous hydrochloric acid solution and extracted with 3×120 milliliter portions of methylene chloride. The combined organic extracts were dried over anhydrous magnesium sulfate, filtered and concentrated in vacuo, affording 6.05 grams of a golden oil confirmed by NMR analysis as the desired product.

EXAMPLE VIII

Preparation of: Alpha-ethoxycarbonyl 5-(2-chloro-4-trifluoromethylphenoxy)-2-nitroacetophenone A mixture of 6.0 grams (0.011 mole) of t-butylethyl 2-[5-(2-chloro-4-trifluoromethylphenoxy)-2-nitrobenzoyl]malonate (prepared as described in Example VII), 100 milliliters of chlorobenzene and 0.2 gram of p-toluenesulfonic acid was heated to reflux and maintained at reflux for about 20 hours. The progress of the reaction being periodically monitored by TLC analysis. The reaction mixture was then allowed to cool to room temperature, was diluted with 100 milliliters of ethyl acetate, washed with 100 milliliters of saturated aqueous sodium bicarbonate solution, and phase separated. The aqueous layer was back extracted with 2×100 milliliter portions of ethyl acetate and the combined organic phases were dried over anhydrous magnesium sulfate, filtered and concentrated in vacuo, affording 5.0 grams of brown, mobil oil confirmed by NMR and MS analyses as the desired product.

Although preparation of certain compounds of the invention have been illustrated in some detail by the foregoing Examples, it is to be understood that other compounds of the invention may be readily prepared by those skilled in the art using the same or similar techniques and by varying the choice of starting materials.

Weed control in accordance with this invention is effected by application, either before or after emergence of weeds, of a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application. The quantity of a compound of this invention applied in order to exhibit a satisfactory herbicidal effect may vary over a wide range and depends on a variety of factors, such as, for example, hardiness of a particular weeds species, extent of weed infestation, climatic conditions, soil conditions, method of application, and the like. Typically, as little as one or less pound per acre of a compound of this invention would be expected to provide satisfactory weed control, although in some instances application rates in excess of one pound per acre; e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.01 to 2.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America*, may be used in combination with a compound or compounds of the invention. Typically such formulations will contain from about 5 to about 95 percent by weight of a compound of this invention.

The herbicidal formulations contemplated herein can be applied by any of several method known to the art. Generally, the formulation will be surface applied as an aqueous spray. Such application can be carried out by conventional ground equipment, of if desired, the sprays can be aerially applied. Soil incorporation of such surface applied herbicides is accomplished by natural leaching, and is, of course, facilitated by natural rainfall and melting snow. If desired, however, the herbicides can be incorporated into the soil by conventional tillage means.

The compounds prepared as described in Examples I were individually screened for herbicidal efficacy, against a variety of broadleaf and grassy weed species, under controlled laboratory conditions of light, humidity and temperature. Solvent solutions of said compound was applied, both preemergence and postemergence, to test flats containing the various weed species, and herbicidal efficacy was determined by visual inspection, after application of the compounds. Herbicidal efficacy was determined on a linear scale of from 0 (no injury) to 10 (all plants dead).

At a screening rate of application of 10 pounds per acre, each of the compounds exhibited very good preemergence control of teaweed, jimsonweed, wild mustard, yellow nutsedge, yellow foxtrail, large crabgrass, Johnsongrass, coffeeweed, velvetleaf, tall morningglory, wild oats and barnyardgrass, injury ratings averaging in the range of 8 to 10 being determined up to 22 days subsequent to application. Each compound also exhibited very good postemergence control, at the rate of 10 pounds per acre screening rate, of teaweed, jimsonweed, wild mustard, yellow foxtail, coffeeweed, velvetleaf, tall morningglory and barnyardgrass, injury ratings averaging in the range of 7 to 10 being determined up to 22 days subsequent to application.

Basis these screening tests, compounds of this invention can be effectively used for preemergence or postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horsetail ironweed, sesbania, cattail, wintercress, horsenettle, nutsedge, milkweed, sicklepod, and the like.

Of course, the invention compounds could be used to effectively control weeds growing amongst crops such as wheat, oats, rice, barley, corn, soybeans, rice, peanuts and the like without causing significant damage to the growing crop.

Although the invention has been described in considerable detail by the foregoing, it is to be understood that many variations may be made therein by those skilled in the art without departing from the spirit and scope thereof as defined by the appended claims.

We claim:

1. A compound represented by the formula:

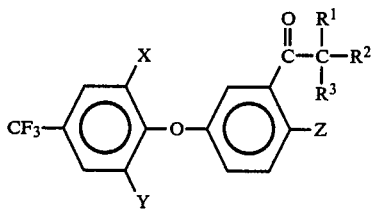

wherein:
X and Y are hydrogen or halogen provided that at least one of X or Y is halogen;
Z is nitro, halogen or cyano; $R^1$, $R^2$ and $R^3$ are individually selected from hydrogen, cyano, up to $C_4$ alkyl, haloalkyl alkoxy or alkoxyalkyl, up to $C_4$ alkenyl or alkynyl, phenyl or phenyl substituted with halogen, cyano, nitro or haloalkyl, provided that at least one of $R^1$, $R^2$ or $R^3$ is $-COOR^4$ wherein $R_4$ is hydrogen, up to $C^4$ alkyl, haloalkyl or alkoxy, mono- or dialkylamino, cyano or an agronomically suitable salt species selected from alkali metal ion, ammonium or substituted ammonium ion.

2. A compound of claim 1 wherein X is fluorine or chlorine; Y is hydrogen; Z is nitro or halogen; and $R^1$, $R^2$ or $R^3$ are hydrogen or $-COOR^4$ wherein $R^4$ is alkyl.

3. A compound of claim 1 selected from diethyl 2-[5-(2-chloro-4-trifluoromethylphenoxy)-2-nitrobenzoyl]-2-methylmalonate; diethyl 2-[5-(2-fluoro-4-trifluoromethylphenoxy)-2-nitrobenzoyl]-2-phenyl malonate; dimethyl 2-[5-(2-chloro-4-trifluoromethylphenoxy)-2-chlorobenzoyl]malonate; ethyl 2-[5-(2-chloro-4-trifluoromethylphenoxy)-2-chlorobenzoyl]cyanoacetate; ethyl 2-[5-(2-chloro-4-trifluoromethylphenoxy)-2-nitrobenzoyl] cyanoacetate; diethyl 2-[5-(2-chloro-4-trifluoromethylphenoxy)-2-nitrobenzoyl]-2-allyl malonate; t-butylethyl 2-[5-(2-chloro-4-trifluoromethylphenoxy)-2-nitrobenzoyl]malonate; and alpha-ethoxycarbonyl 5-(2-chloro-4-trifluoromethylphenoxy)-2-nitro-acetophenone.

4. A compound of claim 3 which is alphaethoxycarbonyl 5-(2-chloro-4-trifluoromethylphenoxy)-2-nitroacetophenone.

5. A herbicidal composition containing an inert carrier and a herbicidally effective amount of a compound or mixture of compounds defined in claim 1.

6. In a method of controlling weeds wherein a herbicidally effective amount of herbicide is applied to a growth medium prior to emergence of the weeds therefrom or the weeds subsequent to their emergence from the growth medium, wherein the improvement resides in using as the herbicide a compound or mixture of compounds defined by claim 1.

* * * * *